United States Patent [19]

Tam

[11] Patent Number: 5,333,164
[45] Date of Patent: Jul. 26, 1994

[54] METHOD AND APPARATUS FOR ACQUIRING AND PROCESSING ONLY A NECESSARY VOLUME OF RADON DATA CONSISTENT WITH THE OVERALL SHAPE OF THE OBJECT FOR EFFICIENT THREE DIMENSIONAL IMAGE RECONSTRUCTION

[75] Inventor: Kwok C. Tam, Schenectady, N.Y.

[73] Assignee: General Electric Company, Schenectady, N.Y.

[21] Appl. No.: 805,163

[22] Filed: Dec. 11, 1991

[51] Int. Cl.$^5$ .......................................... G01N 23/083
[52] U.S. Cl. ........................................ 378/8; 378/14; 378/901; 364/413.15; 364/413.16; 364/413.17
[58] Field of Search .................... 378/4, 14, 8, 901; 364/413.15, 413.16, 413.17, 413.26

[56] References Cited

U.S. PATENT DOCUMENTS

| | | | |
|---|---|---|---|
| 4,375,696 | 3/1983 | Wagner | 378/20 |
| 4,504,909 | 5/1985 | Acharya et al. | 364/414 |
| 5,047,931 | 9/1991 | Lin | 364/413.21 |
| 5,068,882 | 11/1991 | Eberhard | 378/4 |
| 5,073,910 | 12/1991 | Eberhard et al. | 378/4 |
| 5,136,660 | 8/1992 | Flickner et al. | 382/46 |
| 5,170,439 | 12/1982 | Zeng et al. | 382/6 |
| 5,187,659 | 2/1993 | Eberhard et al. | 364/413.15 |
| 5,218,534 | 6/1993 | Trousset et al. | 364/413.17 |
| 5,253,171 | 10/1993 | Hsiao et al. | 364/413.19 |

OTHER PUBLICATIONS

Convolutional Reconstruction From Cone-Beam Projection Data, Gerald N. Minerbo, IEEE Transactions on Nuclear Science, vol. NS-26, No. 2, Apr. 1979, pp. 2682-2684.
Practical Cone-Beam Algorithm, L. A. Feldkamp, L. C. Davis, and J. W. Kress, J. Opt. Soc. Am. A, vol. 1, No. 6, Jun. 1984, pp. 612-619.
P. Grangeat, "Analysis of a 3D Imaging System by Reconstruction from X-Radiographies in Conical Geometry," Ph.D. Thesis, National College of Telecommunications (l'Ecole Nationale Superieure des Telecommuncations), France (1987) [translateion enclosed].
Cone-Beam Tomography: Recent Advances and a Tutorial Review, Bruce D. Smith, Optical Engineering, May 1990, vol. 29, No. 5, pp. 524-534.
Image Reconstruction From Cone-Beam Projection: Necessary and Sufficient Conditions and Reconstruction Methods, Bruce D. Smith, IEEE Transactions on Medical Imaging, Mar. 1985, vol. MI-4, No. 1, pp. 14-25.
An Inversion Formula for Cone-Beam Reconstruction, Heang K. Tuy, Siam J. Appl. Math., Jun. 1983, vol. 43, No. 3, pp. 546-552.

Primary Examiner—Paul M. Dzierzynski
Assistant Examiner—David V. Bruce
Attorney, Agent, or Firm—Paul R. Webb, II

[57] ABSTRACT

An improved method and apparatus is disclosed for retaining only necessary cone beam projection data acquired along a three dimensional scanning trajectory in order to ensure more computationally efficient processing of Radon data for computerized tomographic image reconstruction consistent with the overall shape of an object irradiated by a cone beam source. If the scanning trajectory is such that an otherwise complete see of Radon data is acquired the image so reconstructed will also be exact. The invention is directed to restricting image reconstruction processing to only that region of support in Radon space actually occupied by the object itself; therefore, computational approximations consistent with the overall shape of the object can be applied to improve image reconstruction efficiency.

11 Claims, 6 Drawing Sheets

PART $f(x,y,z,)$

CONE BEAM
DETECTOR DATA $X(\theta) = \int f(r,\theta,z_0)dr$

DETECTOR
INTEGRALS $\int X(\theta)d\theta = \iint f(r,\theta,z_0)drd\theta$

RADON TRANSFORMS $\iint f(r,\theta,z_0)rdrd\theta$

PARALLEL BEAM
DETECTOR DATA $\hat{x}(q) = \int f(x,y,z)ds$

3D CT IMAGE $\hat{f}(x,y,z,)$

METHOD AND APPARATUS FOR ACQUIRING AND PROCESSING ONLY A NECESSARY VOLUME OF RADON DATA CONSISTENT WITH THE OVERALL SHAPE OF THE OBJECT FOR EFFICIENT THREE DIMENSIONAL IMAGE RECONSTRUCTION

CROSS-REFERENCE TO RELATED APPLICATIONS

The invention disclosed and claimed herein is related to the subject matter of the following commonly-assigned patent applications, the entire disclosures of which are hereby expressly incorporated herein by reference:

Co-pending application Ser. No. 07/737,525 filed Jul. 29, 1991 by Kwok C. Tam entitled "METHOD AND APPARATUS FOR ACQUIRING A UNIFORM DISTRIBUTION OF RADON DATA SUFFICIENTLY DENSE TO CONSTITUTE A COMPLETE SET FOR EXACT IMAGE RECONSTRUCTION OF AN OBJECT IRRADIATED BY A CONE BEAM SOURCE";

Co-pending application Ser. No. 07/737,117 filed Jul. 29, 1991 by Kwok C. Tam entitled "METHOD FOR CONSTRUCTING A THREE DIMENSIONAL SCANNING TRAJECTORY CAPABLE OF ACQUIRING A COMPLETE SET OF RADON DATA FOR EXACT IMAGE RECONSTRUCTION OF AN OBJECT IRRADIATED BY A CONE BEAM SOURCE";

Co-pending application Ser. No. 07/725,142 filed Jul. 3, 1991 by Kwok C. Tam entitled "METHOD AND APPARATUS FOR ACQUIRING COMPLETE RADON DATA FOR EXACTLY RECONSTRUCTING A THREE DIMENSIONAL COMPUTERIZED TOMOGRAPHY IMAGE OF A PORTION OF AN OBJECT IRRADIATED BY A CONE BEAM SOURCE";

U.S. Pat. No. 5,257,183, filed Dec. 21, 1990, to Kwok C. Tam, entitled "METHOD AND APPARATUS FOR CONVERTING CONE BEAM X-RAY PROJECTION DATA TO PLANAR INTEGRALS AND RECONSTRUCTING A THREE-DIMENSIONAL COMPUTERIZED TOMOGRAPHY (CT) IMAGE OF AN OBJECT;

Co-pending application Ser. No. 07/631,818, filed Dec. 21, 1990, by Kwok C. Tam, entitled "PARALLEL PROCESSING METHOD AND APPARATUS FOR RECONSTRUCTING A THREE-DIMENSIONAL COMPUTERIZED TOMOGRAPHY (CT) IMAGE OF AN OBJECT FROM CONE BEAM PROJECTION DATA OR FROM PLANAR INTEGRALS";

U.S. Pat. No. 5,073,910, filed Aug. 27, 1990, to Jeffrey W. Eberhard et al, entitled "SQUARE WAVE CONE BEAM SCANNING TRAJECTORY FOR DATA COMPLETENESS IN THREE DIMENSIONAL COMPUTERIZED TOMOGRAPHY";

U.S. Pat. No. 5,068,882, filed Aug. 27, 1990, to Jeffrey W. Eberhard et al, entitled "DUAL PARALLEL CONE BEAM CIRCULAR SCANNING TRAJECTORIES FOR REDUCED DATA INCOMPLETENESS IN THREE-DIMENSIONAL COMPUTERIZED TOMOGRAPHY"; and U.S. Pat. No. 5,270,926, filed Dec. 21, 1990 to Kwok C. Tam, entitled "METHOD AND APPARATUS FOR RECONSTRUCTING A THREE-DIMENSIONAL COMPUTERIZED TOMOGRAPHY (CT) IMAGE OF AN OBJECT FROM INCOMPLETE CONE BEAM PROJECTION DATA".

FIELD OF INVENTION

The present invention relates generally to three dimensional (3D) computerized tomography (CT) and more specifically to an improved method and apparatus for acquiring and/or retaining only necessary cone beam data acquired along a suitable three dimensional scanning trajectory thereby ensuring computationally efficient processing of necessary and sufficient Radon data for exact image reconstruction. Only data corresponding to source beams which actually penetrate the object are retained for computation. The data is retained in a manner consistent with the overall shape of a normal projection of the irradiated object.

BACKGROUND OF THE INVENTION

Conventional CT employs a technique for obtaining cross sectional slices of an object from planar parallel or fan beam irradiation of an object. The technique is primarily utilized in medical and industrial diagnostics. Traditional image reconstruction techniques have been predominantly two dimensional. In three dimensions, an undistorted image of an object can be mathematically reconstructed in an exact manner by back projecting a parallel beam which has been attenuated after passing through an object using an inverse transform based on the Fourier Slice Theorem. The use of a parallel beam source and a flat two dimensional detector geometrically simplifies reconstruction but complicates speed and ease of data collection.

Image reconstruction can be mathematically accomplished for a 3D cone beam source by an inverse Radon transform using suitable planar integrals. These planar integrals are computed from detector integrals which utilize measured cone beam projection data i.e. the detected attenuated intensity representative of the density distributions of the irradiated object. The use of a 3D cone beam source expedites data acquisition, but complicates geometrical considerations when used with a conventional flat array detector.

In two dimensions, the analog of cone beam source geometry is illustrated by tan beam geometry. For the case of two dimensional fan beam geometry, the detector integrals are equivalent to the Radon transform of the object. Unlike the two dimensional case, a direct Radon inversion of three dimensional cone beam data from a cone beam source is not possible. Before the inverse Radon transform can be undertaken in three dimensions, the cone beam detector integrals must be reconfigured into planar integrals suitable for direct inverse Radon transformation. Due to the limitations of direct inversion, three dimensional CT imaging has traditionally involved stacking slices representative of the density distribution through the object obtained from various parallel or fan beam attenuation projections. Each projection is associated with a particular view angle or illumination configuration of source and detector relative to the object. A Radon data set is generally acquired by either rotating a source and detector, fixed relative to one another, around an object taking projections as the object is scanned; or alternatively, rotating the object between the fixed source and detector. Such a Radon data set comprises plurality of discrete data points corresponding to projected attenuated intensity at discrete grid points of an array detector.

Three dimensional Radon inversion is addressed using a two step approach to perform an inverse Radon transform on planar integrals representing cone beam data obtained on a plurality of coaxial planes in Radon space. The first step involves calculating from the planar integrals a two dimensional projection image of the object on each of a plurality of coaxial planes; while the second step involves defining normal slices through these coaxial planes which a two dimensional reconstruction of each slice is obtained. In this slice by slice way, the reconstruction algorithms operate on the plurality of planar integrals to produce a three dimensional image of the object.

The acquired Radon data set is complete only if it provides sufficient Radon data at every necessary point Radon space, i.e. Radon space must be sufficiently filled with data over the region of support in Radon space which corresponds to that region of space occupied by the object in object space. Sufficient filling of Radon space by scanning along a suitable trajectory is necessary for exact image reconstruction. Furthermore, if the detector integral space is filled over the region of support for the object, the Radon data set is said to be complete. Bruce D. Smith in an article entitled "Image Reconstruction from Cone-Beam Projections: Necessary and Sufficient Conditions and Reconstruction Methods," IEEE Trans. Med. Imag., MI-4 (1985) 14, describes a cone beam data set as 'complete' if each plane passing through the object cuts the scanning trajectory in at least one point. This criterion assumes that the detector is fixed relative to the source and that the entire object can be scanned in a continuous manner within the field of view of the source beam. Depending on the scanning trajectory employed to obtain the cone beam projection data, the acquired data set in Radon space may or may not be complete. Data collected using a commonly adopted single circular scan is incomplete and artifacts may accordingly be introduced into the reconstructed image. Dual parallel circular scanning trajectories have been shown to reduce data set incompleteness. A circular square wave scanning trajectory, as well as, dual mutually perpendicular circular scanning trajectories provide a complete Radon data set for exact image reconstruction having been shown to satisfy the completeness criterion as articulated by Smith. More recently, Bruce D. Smith in article entitled "Cone-beam Tomography: Recent Advances and a Tutorial Review", Optical Engineering, Vol. 29, No. 5, pp. 524-534, May 1990, mentions several complete scanning trajectories.

The volume of Radon space must not only be filled in a sufficiently dense manner to accommodate unique reconstruction from a complete data set; but, Radon data must also be acquired in a substantially uniform manner to reflect consistency in the inversion process. This too is accomplished by employing suitable sampling about an appropriate scanning trajectory.

Utilizing an incomplete and/or non-uniform data set for image reconstruction by Radon inversion introduces artifacts which compromise image quality and may render the image inadequate for medical or industrial diagnostic use. The density of acquired Radon data, the distribution of this density, and the volume of data obtained all contribute to the accuracy and efficiency of image reconstruction. Generally, choice of scanning trajectory is the only major consideration regarding data acquisition. Radon data is typically acquired throughout the whole of Radon space, without regard to any apriori selectivity as to what data is necessary based on the shape and character of the object being scanned. Proper dana acquisition typically involves acquiring a complete data set throughout all of Radon space having sufficiently dense information to accurately reconstruct the image in a uniform manner. Sampling conventions are generally only concerned with location, i.e. where to scan for data, and step size, i.e. how far apart data should be sampled along a scan path.

It would be desireable for data acquisition and sampling to proceed in a more computationally expedient manner wherein data is acquired and/or retained nor only a necessary volume of Radon space. According to this invention, the necessary volume of Radon space to be filled is predetermined in an apriori manner accorded by the shape of the object and implemented into a data collect ion and/or retention scheme. Such apriori selectivity can reduce unnecessary, redundant computational requirement by eliminating the need to fill regions of Radon space with unnecessary data. The collect of only necessary and sufficient Radon data for exact reconstruction without unnecessarily over-burdening computational requirements has not been addressed in the prior art. Using apriori information relating to the shape of the object irradiated within the field of view of the irradiating source eliminates unnecessary computational requirements by simply disregarding that data which is not necessary.

SUMMARY

In accordance with the invention, an object occupies a specified region of support in object space corresponding to a region of support in Radon space from which image reconstruction is performed using a Radon inversion technique. This region of support in object space is delimitted by the shape off the object. Accordingly, restricting image reconstruction processing to only this delimitted region of support in Radon space necessary accommodates a requisite core number of non-redundant computations; wherein the overall shape of the object determines the extent of the required computational grid. Restricting computational processing requirements is further accomplished not only by using the overall shape of the illuminated object to dimensionally truncate the grid within which the three dimensional image of the object is reconstructed but by selectively varying the distribution of grid points within this truncated grid in accordance with the shape of the object.

In the preferred embodiment of the invention, a Radon transform of the object is computed from cone beam planar projection data and an image of the object is reconstructed in a point by point manner from the Radon transform of said data via an inversion process. A projection data set corresponding to the field of illumination containing the object is obtained by scanning at a plurality of positions along a scanning trajectory to acquire a corresponding plurality of discrete cone beam projection data for each planar array detector position. The cone beam projection data is converted to a corresponding plurality of detector integrals. Upon Radon transformation of the detector integrals a corresponding plurality of Radon data points is organized onto coaxial planes in Radon space. Each coaxial plane comprises a polar grid of Radon data points. The attenuation of the object when sampled on a particular plane is equivalent to the two dimensional normal projection of the object onto that plane. Two dimensional projection data is then reconstructed from the Radon data set of corresponding one dimensional projections at all angles comprising a polar grid of Radon data on the plane. Cone beam attenuation data are sampled by a planar array detector which scans about the illuminated object along a predetermined trajectory at predetermined intervals. Upon suitable transformation the data set obtained by such sampling provides a plurality of coaxial planes, each having a corresponding polar grid of Radon data points exhibiting uniform angular spacing of equal grid segments at all angles. Restricting angular data sampling of each polar grid of data to the acquisition of points actually inside the normal projection of the object's region of support in Radon space allows only cone beams which actually penetrate the object to be acquired and/or retained for data processing in accordance with the invention. This restricts data acquisition and/or retention in Radon space to a grid of data points truncated by the projected overall shape of the object. For the case of a substantially flat object, extending much less in one dimension than in the other two, data acquisition is further restricted by applying angular approximations consistent with the shape of the object resulting in coatset angular sampling in the shorter dimension of the substantially flat object. Thus, the shape of the object dictates customized sampling of a smaller, truncated grid of data points which represent only source beams which actually penetrate the object. These restrictions in data acquisition and/or retention result in substantial savings in computation and memory requirements; thus, faster computing times are achieved.

OBJECTS OF THE INVENTION

It is an object of this invention to reduce the number of requisite computations by eliminating the processing of unnecessary data thereby reducing memory storage requirements and speeding up image processing time.

It is another object of the invention to provide an exact 3D cone beam reconstruction image of a substantially flat object, or an object capable of accommodating like approximation.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings in which:

DETAILED DESCRIPTION OF THE INVENTION

Figure 1:
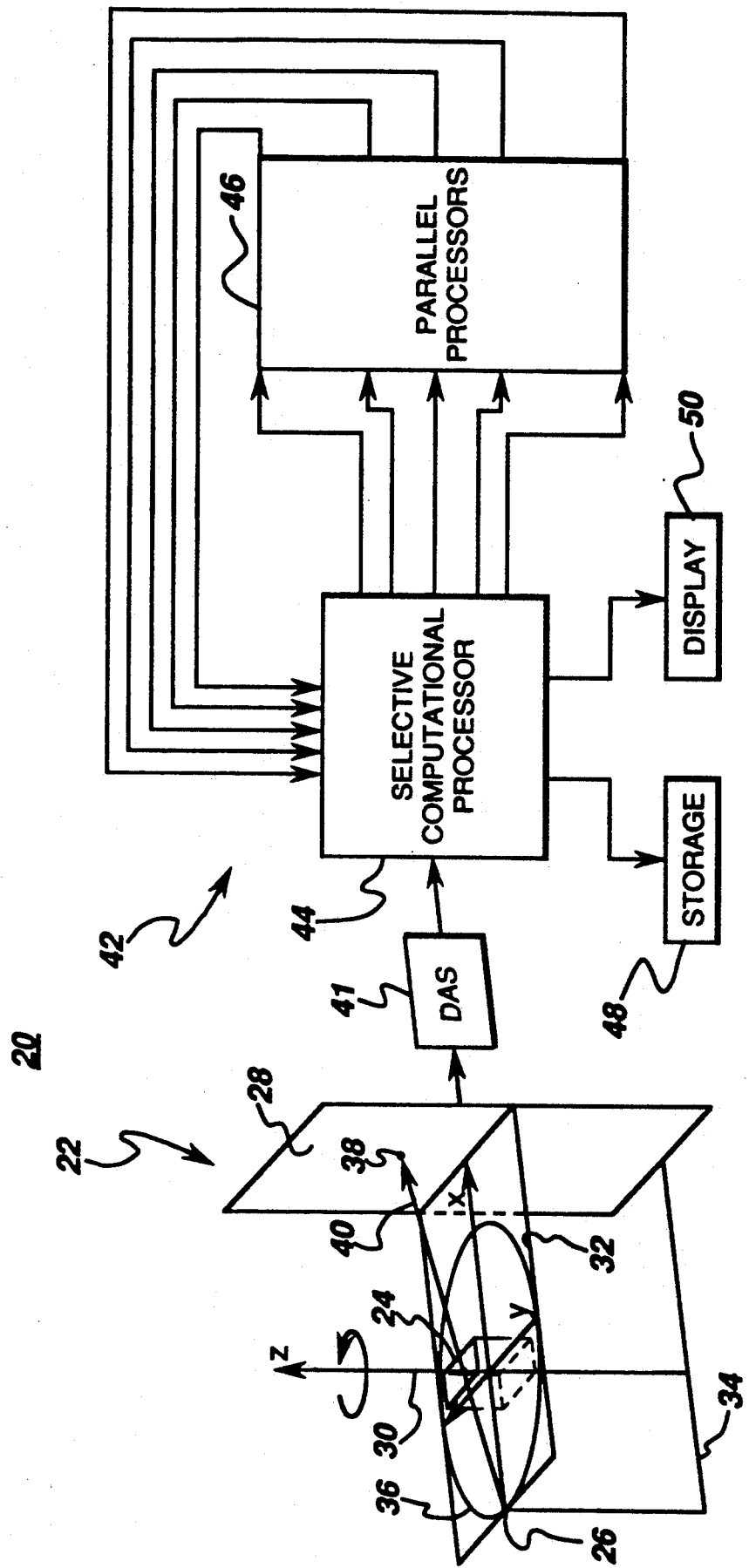
FIG. 1 is a schemmatic diagram of a three dimensional CT scanning and Radon inversion processing apparatus to acquire and efficiently process only necessary Radon data in accordance with the invention.

FIG. 1 is a schemmatic diagram of a three dimensional CT scanning and data processing system 20 apparatus in accordance with the invention. A three dimensional CT scanning portion 22 of apparatus 20 employing cone beam geometry is shown with an object 24 positioned within the field of view between an irradiating source 26 and a typical two dimensional detector array 28, in order to provide source beam projection data. An axis of rotation 30 passes through the field of view and object 24. For purpose of analysis, a midplane 32 is defined normal to the axis of rotation 30 which contains the irradiating source 26. By convention, axis of rotation 30 is generally taken to be the z axis, having its origin at its intersection with the midplane. The (x,y,z) coordinate system is fixed relative to the source 26 and array detector 28. In scanning the object 24 at a plurality of angular positions, a scanning mechanism 34 causes the source 26 to move relative to object 24 and the field of view typically rotates along a circular scanning trajectory 36 lying in the midplane 32, while the array detector 28 remains fixed with respect to source 26 (or alternatively object 24 can be rotated while the source 26 and array detector 28 remain stationary). Data is discretely acquired at a plurality of source positions during the scan. Only a select subset of the input data collected at array detector 28 represent line integrals of the attenuated intensity of source beams actually passing through object 24. Other beams never penetrate object 24. The typical approach to reconstruction has previously embodied calculating planar integrals corresponding to each and every detector line integral, without regard to identifying which of these actually penetrate object 24, on a set of coaxial planes; then performing an inverse Radon transform on each and every planar integral after suitable conversion to reconstruct a three dimensional image of the object. In accordance with the invention, only a select subset of data 38 representing attenuation of source beams 40 actually passing through object 24 will be retained in data acquisition system 41 as a truncated Radon data set representing those data necessary to reconstruction of the 3D object image. System 41 is operatively connected to array detector 28 and to a suitable data acquisition and data processing portion 42 of apparatus 20. Portion 42, wherein reconstruction of object 24 is accomplished, comprises a selective computational processor 44, usually represented as a computer, to which system 41 is operatively connected; a plurality of dedicated 2D CT reconstruction parallel processors 46; a representative storage device 48 comprising mass storage and RAM, for example; and a suitable output device represented as display 50. The selective computational processor 44 receives beam attenuation data from data acquisition system 41, to selectively distribute data among and to receive data from the plurality of dedicated parallel processors 46; to utilize storage device 48; and to provide output to display 50. The plurality of parallel processors 46 preferably comprise specialized array processors for doing filtered backprojection to reconstruct 2D images, such as the STAR processor used in the General Electric CT scanners. Selective computational processor 44 computes planar integrals from respective line integrals associated with detected attenuated intensity 38 of source beams 40 which have actually passed through object 24 and then sort them onto a predetermined set of planes in Radon space coaxial with reference axis 30.

In accordance with the invention only a necessary plurality of planar integrals representing source beams attenuated by actually penetrating the object are acquired and/or retained. This comprises a truncated Radon data set representing only that data necessary for reconstructing the 3D image of the object. Selective computational processor 44 operates to distribute planar integrals onto the plurality of coaxial planes using dedicated 2D CT reconstruction parallel processors identified collectively at 46. In each parallel processor, a two dimensional image of only the object as projected onto each plane is reconstructed from the selectively acquired and/or retained input planar integrals corresponding to that plane. This operation proceeds independently for each plane in a parallel manner. The plurality of 2D projection images of only the object are then returned to selective computational processor 44 which organizes these projection images onto yet another plurality of planes defined as slices perpendicular to the reference axis of the coaxial set of planes. A corresponding image of only the object on each slice is reconstructed from line integrals corresponding to that slice. The organization of this data now accomodates direct reconstruction by Radon inversion. Selective computational processor 44 then operates to distribute these images now organized as slices among a select plurality of 2D CT reconstruction processors 46. These processors operate in parallel to again independently reconstruct corresponding image slices from input line integrals on the same plane. The resultant 2D image slices when taken together represent the three dimensional image of only object 24 and as such are routed back through selective computational processor 44 for display 50 and/or storage 48.

Figure 2A:
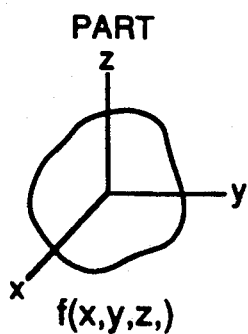
FIGS. 2a-2f diagram a generalized Radon transform computational method for three dimensional CT image reconstruction in accordance with the present invention.
Figure 2B:
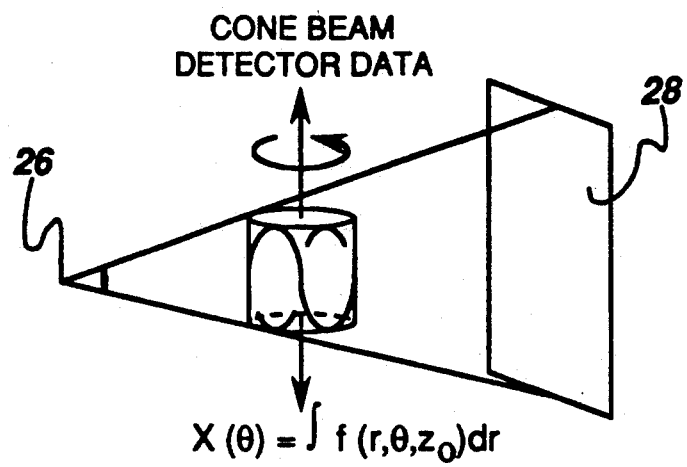
Figure 2C:
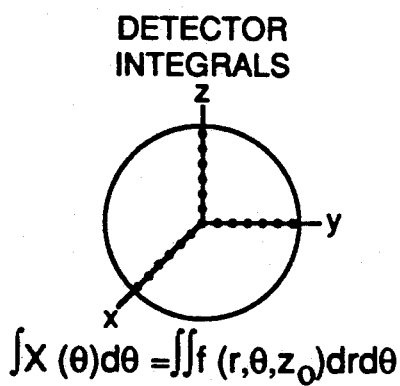
Figure 2D:
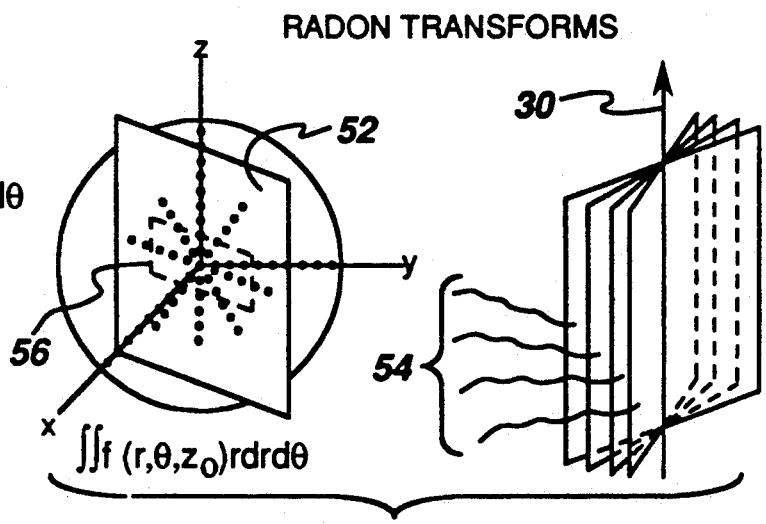

A generalized Radon transform computational method for three dimensional CT imaging is illustrated in FIGS. 2a through 2f identifying at FIG. 2d that step of the method improved in accordance with the present invention. This computational method is undertaken in a point by point manner. A point occupied by the object itself is defined in terms of its attenuation coefficient f(x,y,z) as seen in FIG. 2a. The measured cone beam projection data then corresponds to an integral of this attenuation function about a scanning trajectory as shown in FIG. 2b where 26 indicates the cone beam source and 28 indicates the planar array detector. Attenuation data is acquired on array detector 28 at various positions along the source scanning trajectory (not shown). This corresponds to a plurality of planes of cone beam projection data points. The corresponding detector integrals are represented as integrals of the cone beam projection data which in three dimensions correspond to surface integrals of attenuation as seen in FIG. 2c. For a cone beam source, the Radon transform is mathematically identified in FIG. 2d wherein data points in Radon space are illustrated. Mathematically, the Radon transform differs in form from the mathematical form of the detector integral identified in FIG. 2c by a factor of "r". Radon space must be filled with data points over a region of support in Radon space which corresponds to the field of view in object space within which the object being scanned resides. Conventionally, Radon data is taken to fill the whole extent of available Radon space.

In accordance with the invention, at the step in the method identified at FIG. 2d, only Radon data representative of source beams actually penetrating the object are selectively acquired and/or retained for further processing. Thus, Radon space is represented by a truncated data set of discrete Radon data points wherein truncation indicated by dotted lines at 56, which are organized onto a plurality of planes 54 coaxial about the z-axis 30. Each such plane is organized into a polar grid of data points 52 in Radon space. In accordance with the invention, each polar grid is truncated according to the 2D projection 56 of object 24 onto that plane. Accordingly, cone beam projection data is acquired from a plurality of scanning positions of array detector plane 28, then transformed and organized for selective acquisition and/or retention via a plurality of polar grids of Radon data points 52 which are truncated in accordance with the projected shape 56 of object 24. Only this truncated Radon data set is further computationally manipulated in a point by point manner to generate a 3D reconstructed image of object 24.

Figure 2E:
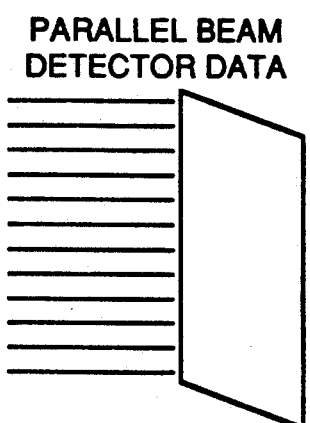
Figure 2F:
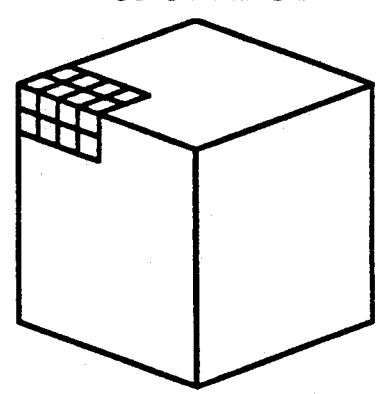

FIGS. 2e and 2f illustrate further point by point Radon inversion processing for reconstructing an image from the retained detector integrals for the simpler case of a parallel beam source which inverts directly, i.e. no intermediate conversion step being required as with cone beam geometry. The three dimensional cone beam inversion process, analogous to FIGS. 2e and 2f, is considerably complicated by imposing a dimensional requirement that each point in Radon space represents a surface integral and further complicated due to the intermediate conversion required to accommodate the process of Radon transform inversion.

Figure 3:
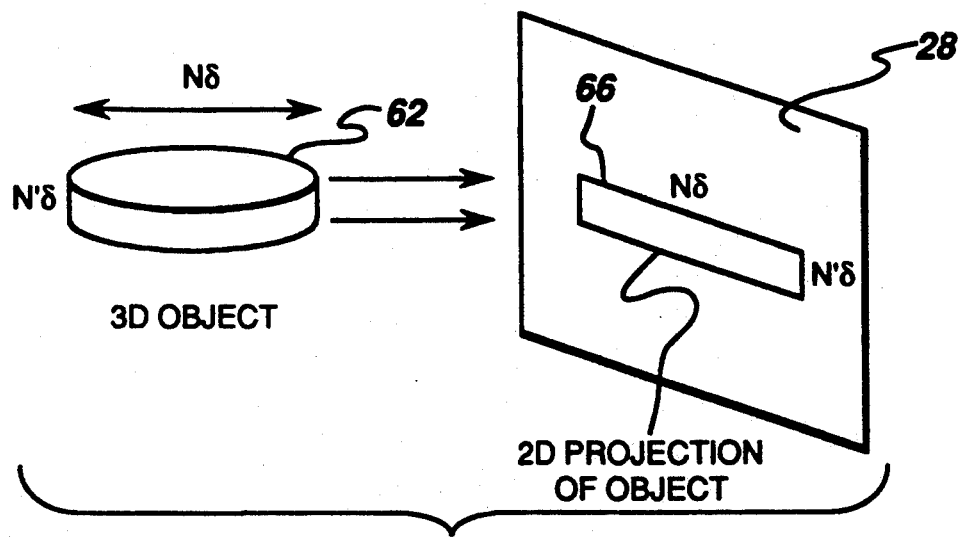
FIG. 3 illustrates a planar projection of a flat object utilized to define a necessary subset of data points on one of a plurality of planes in accordance with the invention.

FIG. 3 shows a flat three dimensional object 62 whose cross section is a circle of radius $N\delta/2$ having a height of $N'\delta$, where $\delta$ indicates the dimension of each cell comprising a uniformly gridded array, while N and N' indicate the number of gridded data points in each respective direction. Typically reconstruction of the image of an object is undertaken on a uniform, cubic $N \times N \times N$ array of data grid points, with only the central $N \times N \times N'$ sub-array actually occupied by the object, leaving the rest of the $N \times N \times N$ array empty. Image reconstruction in this manner unnecessarily overutilizes computer storage resources by storing a reconstruction array much larger than the size of the object and correspondingly wastes computer time by needlessly executing reconstruction operations for array elements not occupied by the object. A grid element specifically utilized for image reconstruct ion is preferably referred to as a voxel, where $\delta$ now defines the voxel dimension. FIG. 3 illustrates a flat object 62, an object that extends much less in one dimension than in the others i.e. N>>N', normally projected onto one plane 28 of a plurality of gridded planes resulting in a rectangular projection 66 of dimension Nδ×N'δ.

Figure 4:
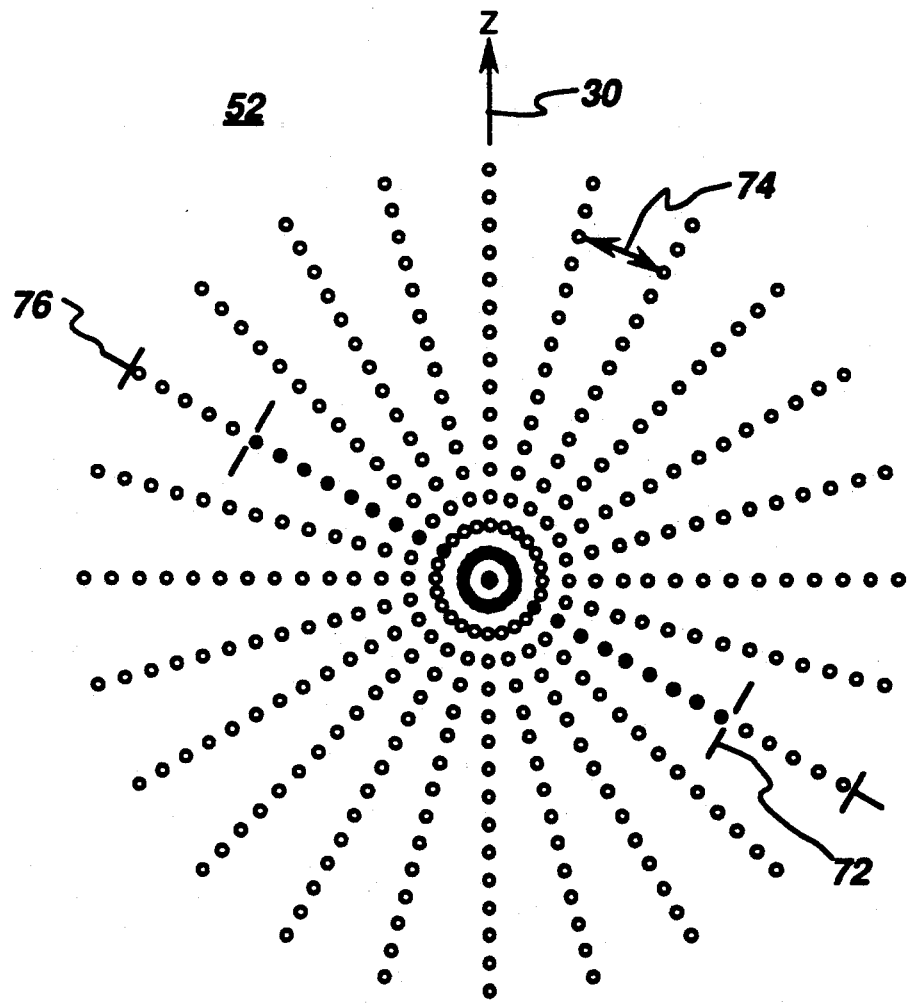
FIG. 4 illustrates a typical polar grid of Radon data points corresponding to one dimensional projection data points occupying the whole extent of available Radon space.

FIG. 4 illustrates a typical, correspondingly uniform, polar grid 52 of Radon data points consisting of an array of one dimensional projections which represent line integrals evaluated at every available grid or data point. The polar grid is comprised of discrete one dimensional projections radially organized into segments 76 which are typically of the same length exhibiting uniform angular distribution in the plane of the page. From this radially symmetric two dimensional polar grid of Radon data points comprising one dimensional line integrals, a two dimensional projection image is reconstructed. A common reference axis 30 (the z axis) passes diametrically through the center of the polar grid. Typically, cone beam data are sampled and one dimensional projections are correspondingly generated on such a polar grid of data points as shown in FIG. 4; wherein the uniform angular spacing of the grid 74 is typically given by $\Delta\theta = 1/\sqrt{2}N$ and radial grid segment lengths 76 are typically given by $s(\theta) = \sqrt{2}N\delta$. On each grid segment the one dimensional projections are sampled at intervals of δ corresponding to a grid or voxel dimension. Using such a sampling scheme the number of grid points required for the plane is therefore given by $2\pi N^2$. Such a uniform radial grid sampling is particularly well suited to centrally localized objects having substantially radial symmetry. If the object does not fill the whole of Radon space a substantial number of the grid points have zero data values and are therefore redundant. Consider for example segment 76 wherein only a length 72 of segment 76 is occupied by necessary data.

Figure 5:
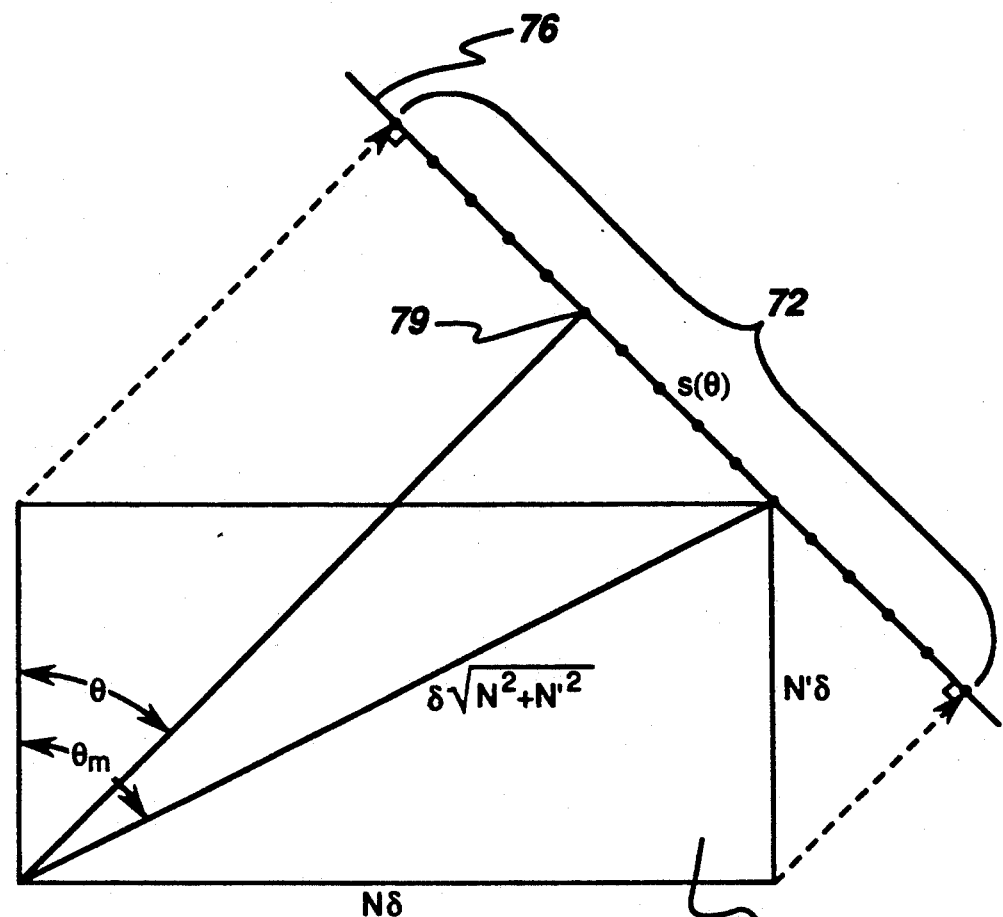
FIG. 5 illustrates selective acquisition and/or retention of only necessary projection data points by truncating segments of the polar grid of FIG. 4 in accordance with the planar projection of FIG. 3.

Consider now the acquisition of cone beam projection data for the substantially flat object 62 of FIG. 3. Radon data is correspondingly acquired along a segment of the polar grid corresponding to plane 28 of FIGS. 1, 2b and 3. Angular spacing and segment length depend on the angle θ formed between the radial grid segments. In FIG. 5, S(θ) represents the length of a linear projection 72 of planar projection 66 onto line 76; wherein planar projection 66 is one projection of flat object 62 onto plane 28 of a plurality of such planes. S(θ) 72 occupies only some portion of grid segment 76 as suggested in FIG. 4, this segment corresponds to planar projection 66 of flat object 62 thereon as suggested in FIG. 3.

From FIG. 5 and geometry it can be shown that S(θ) can be expressed as the following:

$$S(\theta) = \delta(N \cos \theta + N' \sin \theta) \quad (1)$$

wherein $$\theta \epsilon \left(0, \frac{\pi}{2}\right)$$

defines angular displacement through a normal projection 66 of object 62. In the partial angular range given by $\theta\epsilon(0,\theta_m)$ where $\theta_m = \tan^{-1}(N/N')$, segment 72 obtained by normal projection through object 62 is approximated by $$S(\theta) \approx \delta N \cos \theta \text{ where } N>>N' \quad (2)$$

In the angular range given by $$\theta \epsilon \left(\theta_m, \frac{\pi}{2}\right)$$

normal projection segment 72 is approximated by:

$$S(\theta) \approx \delta N' \sin \theta \to \delta N' \text{ as } \theta \to \frac{\pi}{2} \quad (3)$$

This establishes the portion 72 of each grid segment 76 which contains necessary data to be retained for computation.

Likewise angular spacing can be shown from geometry to be given by:

$$\Delta\theta = \frac{\cos \theta}{N} \text{ for } \theta\epsilon (0,\theta_m) \quad (4)$$

and $$\Delta\theta = \frac{1}{N} \text{ for } \theta\epsilon \left(\theta_m, \frac{\pi}{2}\right). \quad (5)$$

The number density of radial array segments per unit angle is then given by:

$$f(\theta) = \frac{1}{\Delta\theta} = \frac{N}{\cos \theta} \text{ for } \theta\epsilon (0,\theta_m) \quad (6)$$

and $$f(\theta) = N \text{ for } \theta\epsilon \left(\theta_m, \frac{\pi}{2}\right) \quad (7)$$

Thus, for a flat object, the polar grid of data points is truncated just as polar grid segment 76 is truncated to S(θ) as indicated at 72 of FIG. 5.

Figure 6:
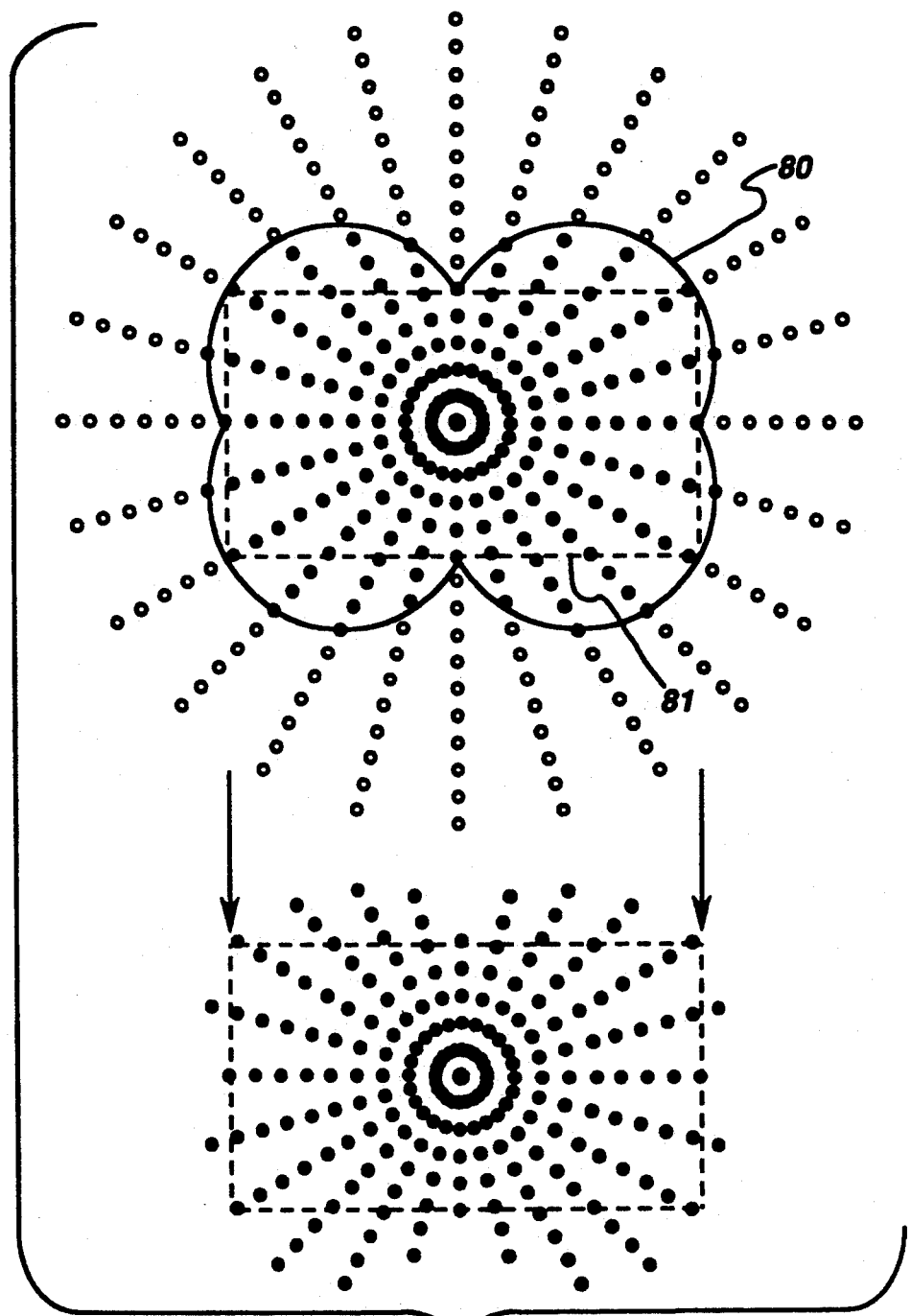
FIG. 6 illustrates the application of the resultant polar grid segment truncation of FIG. 5 to the entire polar grid of FIG. 4 to provide a truncated polar grid accordance with the invention.
Figure 7:
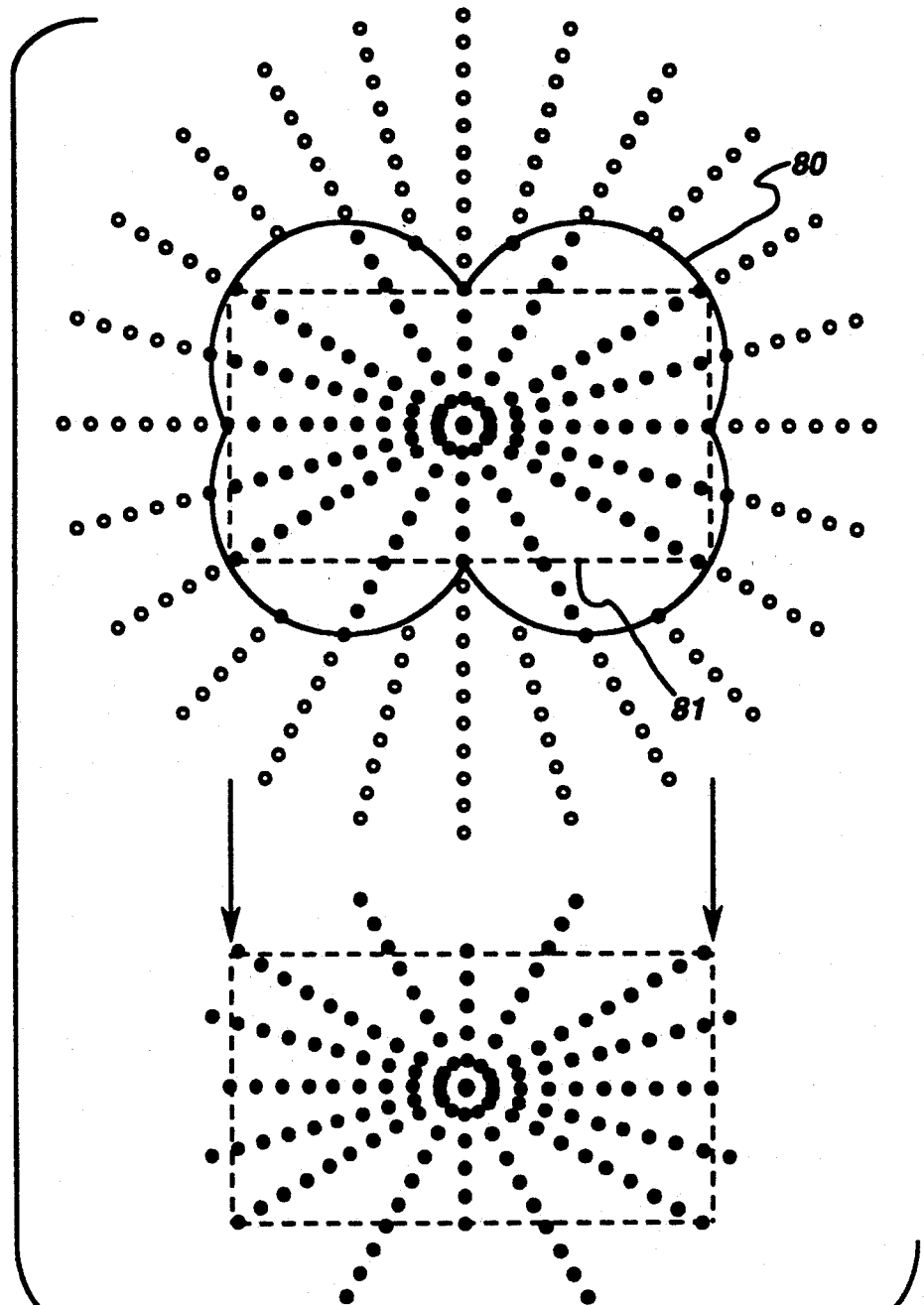
FIG. 7 illustrates customizing the angular distribution of data points within the truncated polar grid of FIG. 6 based on the shape of the object in accordance with the invention.

The resultant truncated grid shown in FIG. 6 comprises a plurality of truncated segments (S(θ)) representing linear projections of a corresponding plurality of planar projections of object 62. The truncated grid is identified by darkened dots against a conventional grid of empty dots; wherein truncation occurs at the boundary depicted by solid line 80, according to the method of FIG. 5. For ease of visualization the boundary of the object, in object space, has been indicated by broken line 81. Furthermore, for a substantially flat object, the angular distribution of truncated polar grid segments can be characterized by more widely spaced shorter grid segments near the vertical and more narrowly spaced longer grid segments near the horizontal as shown in FIG. 7. FIG. 7 shows this re-distributed truncated grid of darkened dots against a conventional polar grid of empty dots for comparison. FIG. 7 illustrates truncation of a conventional polar grid to accomodate not only the shape of object 62, as in FIG. 6, but also a 'flatness' characterizing the shape of object 62. In this way, the distribtution of truncated polar grid segments is customized to accomodate actual shape of object 62. For the case of a flat object, this amounts to providing coarser angular sampling in the short dimension. Therefore; the grid segment length at each angle is chosen to accomodate the shape of the coaxial planar projection of the object's region of support in Radon space, and the angular spacing is chosen consistent with sampling that projected shape. Only Radon data represented by the truncated portion, i.e. just the solid dots, are retained for further computation as indicated in both FIGS. 6 and 7.

Thus, in accordance with the invent ion, computational reconstruction accommodates coarser angular spacing in the direction of the shorter dimension in the region occupied by a flat object. As long as $N>>N'$ is valid, i.e. the object is relatively flat, the approximations of equations 1 through 7 are used to truncate the polar grid of projected data points. Only polar grid data points corresponding to spatial points physically occupied by the object are acquired and/or retained for computation. Furthermore, those polar grid data points acquired and/or retained are sampled within the truncated portion in a manner customized by making approximations consistent with the shape of the object.

Based on the foregoing equations, the number density of data grid points in the angular range given by $\theta\epsilon[0,\theta_m]$ is given by $S_1$ where $$S_1 = \frac{1}{\delta} \int_0^{\theta_m} S(\theta) f(\theta) d\theta = NN'\theta_m \tag{8}$$

Correspondingly, the number density of data grid points in the angular range given by $\theta\epsilon(\theta_m, \pi/2)$ is given by a similar integral, $S_2$, where $$S_2 = \frac{1}{\delta} \int_{\theta_m}^{\frac{\pi}{2}} S(\theta) f(\theta) d\theta = NN' \left( \frac{\pi}{2} - \theta_m \right) \tag{9}$$

Therefore, the total number of data grid points is given by S where $$S = 2(S_1 + S_2) \tag{10}$$

where a 2 has been introduced due to symmetry. Therefore $$S = NN'\pi \tag{11}$$

For the sake of illustration, consider a data grid where $N=512$ and $N'=50$, the number of data points required for image reconstruction on an $N \times N \times N$ array is 1,647,099 where reconstruction on an $N \times N \times N'$ array in accordance with the invention requires only 80,425 data points amounting to about a 95% savings in computer storage requirements.

Figure 8:
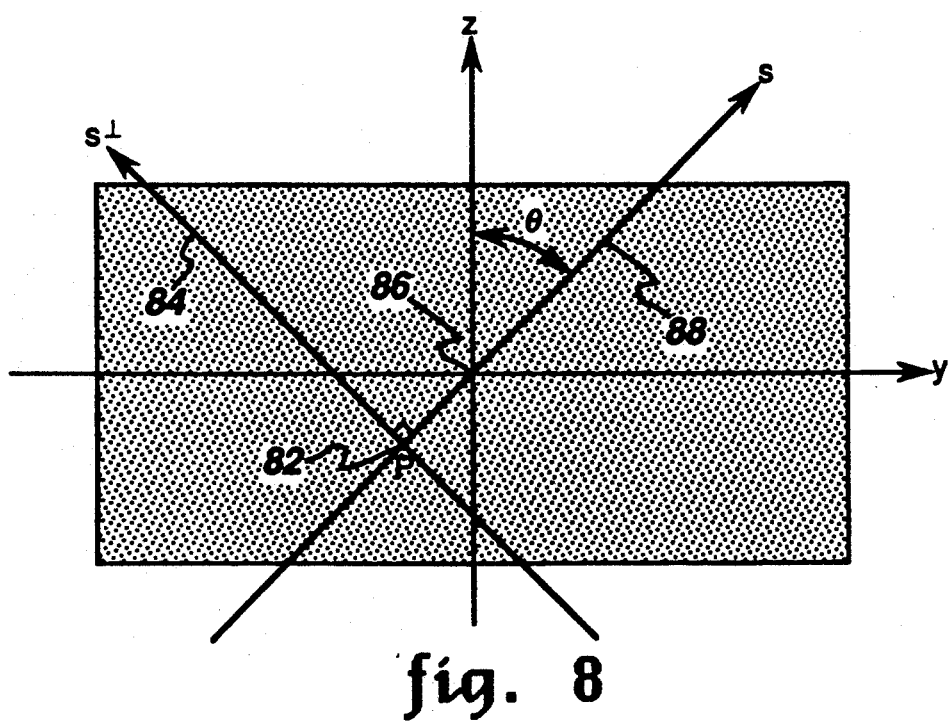
FIG. 8 illustrates the calculation of a single Radon datum at a representative data point within a flat object.

In FIG. 8 a point P is identified at numeral 82 on a vertical plane whose normal is directed in the same direction as a unit vector in the $\phi$ direction in Radon space. The Radon datum at 82 is computed by taking a one dimensional integration (a line integral) on the corresponding cone beam projection image over the line $S^\perp$ identified at 84 which is normal to a line segment taken from the object centered origin 86 to point P at 82. The total number of discrete computations involved in this line integration corresponds to the number of discrete data grid points on the line $S^\perp$ that are within the cone beam projection image.

The total number of computations for all discrete data points 82 along line $S(\theta)$ 88 in the vertical plane of the page corresponding to a constant $\phi$ is proportional to $$M(\theta,\phi) = \int ds \int ds^\perp \tag{12}$$

which is just the area of the planar projection of the region of support of the object in Radon space, in accordance with this invention.

The total number of computations on a particular $\phi$ plane is therefore proportional to $$M(\phi) = \int_0^{\pi} M(\theta,\phi) d\theta = N_\theta NN' \tag{13}$$

where $N_\theta$ is the number of grid lines on each vertical plane.

In practice the line integral over line 84 is performed on cone beam projection data. Since the area of a parallel beam projection image of the region of support of the object is approximately proportional to that of a cone beam projection image, the above relationships are valid. Thus, in the intermediate step of image reconstruction wherein parallel beam images are projected onto coaxial vertical planes, the above relationships of equations 1-13 can be utilized.

In so doing, the number $N_\theta$ of grid lines is given by $$\begin{aligned} N_\theta &= 2 \left[ \int_0^{\theta_m} f(\theta) d\theta + \int_{\theta_m}^{\frac{\pi}{2}} f(\theta) d\theta \right] \\ &= 2 \left[ N'\ln\left( \frac{\sqrt{N^2 + N'^2} + N}{N'} \right) + N\left( \frac{\pi}{2} - \tan^{-1}\frac{N}{N'} \right) \right] \end{aligned} \tag{14}$$

This expression for the number of grid lines can be compared to the number of grid lines for an $N \times N$ image computed in the conventional manner from $f(\theta) = 1/\Delta\theta = \sqrt{2}N$ wherein $$N_\theta = 2 \int_0^{\frac{\pi}{2}} f(\theta) d\theta = \sqrt{2}\, \pi N \tag{15}$$

Using the same numbers utilized in the previous illustration i.e. $N=512$ and $N'=50$ results in $M(\phi) = 5.82 \times 10^7$ for conventional image reconstruction using equations 13 and 15. In accordance with the invention, $M(\phi) = 1.03 \times 10^7$ using equations 13 and 14. Thus, computational requirements for image reconstruction in accordance with the invention are only approximately 18% of those required by conventional methods.

The total number of computations for all $\phi$ planes is then proportional to:

$$\begin{aligned} M &= N_\phi M(\phi) \\ &= N_\phi N_\theta NN' \end{aligned} \tag{16}$$

Figure 9:
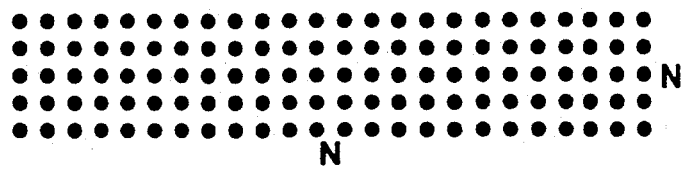
FIG. 9 illustrates a resultant requisite core of projection data points obtained by truncation and redistribution consistent with the overall shape of the object obtained in accordance with the invention.

Finally, Radon inversion proceeds in two steps in which the first step is a parallel beam projection image of the region of support of the object onto co-axial vertical planes requiring only an $N \times N'$ array as illustrated in FIG. 9. This represents an $N'/N$ reduction in conventional N×N array requirements; thus, a corresponding reduction in computational efficiency. An image of the object is then reconstructed in a second step on a set of N' horizontal planes using the digital images reconstructed from the previous step. This preserves the N'/N reduction conventional N×N×N array computational requirements.

The method and apparatus disclosed herein can be modified to accommodate reductions in any dimensional degree of freedom which might be chosen to describe the three dimensional grid corresponding to an object's region of support in Radon space. However, the shape of the object must be such that the object's extent in one dimension is greatly exceeded by the other two to apply the approximations made herein. However, other approximate relationships can be derived to accomodate object shapes other than strictly flat objects and are thus, within the scope of this invention. The invention is particularly suited to medical or industrial imaging of relatively thin sections of an object.

While specific embodiments of the invention have been illustrated and described herein, it is realized that numerous modifications and changes will occur to those skilled in the art. It is therefore understood that the appended claims are intended to cover all modifications and changes as fall within the true spirit and scope of the invention.

What is claimed is:

1. A method for reconstructing an image of a three dimensional object using an inverse Radon transform comprising the steps of:
   providing a mutually spaced irradiating beam source and a suitable array radiation detector in fixed relationship to one another;
   providing an object therebetween;
   irradiating said object within a field of view of said irradiating beam source;
   scanning said irradiated object along a preselected scanning trajectory to acquire a plurality of beam attenuation data at said array detector for a plurality of select source positions;
   organizing said beam attenuation data in the form of line integrals through said object for each of said plurality of source positions;
   determining from said beam attenuation data values representing planar integrals;
   organizing said planar integrals onto discrete polar grids on a predetermined plurality of planes coaxial with respect to a reference axis in Radon space;
   retaining on each said plane only evaluated planar integral values residing within a corresponding overall projected region of support of said object in Radon space in order to truncate each said polar grid to represent source beams actually penetrating said object;
   reconstructing a two dimensional projected image of said object onto each said plane from said retained integral values using parallel processing;
   organizing said plurality of two dimensional projection image data from said plurality of coaxial planes onto a plurality of planes slicing normally through said reference axis; and
   reconstructing two dimensional images on each planar slice using parallel processing to collectively provide a three dimensional reconstructed image of said object.

2. Method according to claim 1 wherein said detector comprises a planar detector.

3. Method according to claim 1 wherein said preselected scanning trajectory is selected to ensure the acquisition of a uniform distribution of Radon data.

4. Method according to claim 1 wherein said scanning trajectory provides a complete set of Radon data for exact image reconstruction from normal projection data.

5. Method according to claim 1, wherein the step of retaining only evaluated planar integral values residing within the overall shape of the projected region of support of the object further comprises making applicable computational approximations in redistributing retained Radon data consistent with the overall shape of the object.

6. Method according to claim 5 wherein the overall shape of the object being substantially flat extends much less in one dimension than in any other orthogonal dimension.

7. An apparatus for acquiring and processing only necessary Radon data for image reconstruction of a three dimensional object irradiated by a mutually spaced scanning source having improved computational efficiency, said apparatus comprising:
   a radiation beam source;
   array radiation detector means fixed with respect to said mutually spaced source;
   means for scanning said irradiated object along a preselected scanning trajectory by rotating said object relative to said mutually spaced source;
   detector means providing a plurality of source beam attenuation data corresponding to a plurality of source positions;
   means for acquiring said plurality of source beam attenuation data;
   means for selective computational processing reconstructing a three dimensional image of said object by a Radon inversion technique;
   said processing means selectively retaining a truncated Radon data set representing a subset ot source beam attenuation data wherein said beams actually penetrate the object;
   said processing means including means for suitably organizing and redistributing computational processing said truncated data set to provide faster parallel processing;
   a plurality of parallel processors for converting said plurality of source beam attenuation data into a corresponding plurality of planar integrals in Radon space subset therof being retained as said truncated Radon data see for computationally reconstructing only Radon data necessary for image reconstruction of said object alone;
   means for storing and retrieving computations; and
   means for displaying computations.

8. Apparatus according to claim 7 further comprising cone beam radiation source.

9. Apparatus according to claim 7 further comprising planar detection means.

10. Apparatus according to claim 7 wherein said scanning trajectory acquires a complete set of Radon data exact image reconstruction.

11. Apparatus according to claim 7 wherein said means for data acquisition comprises means for discretely sampling select projection data to provide a uniform distribution of Radon data.

* * * * *